United States Patent
Marbet et al.

(10) Patent No.: US 10,143,798 B2
(45) Date of Patent: Dec. 4, 2018

(54) LIQUID STORAGE AND DELIVERY SYSTEM

(71) Applicant: SENSILE MEDICAL AG, Olten (CH)

(72) Inventors: Regina Marbet, Rütschelen (CH); Alexandre Perrier, Liestal (CH)

(73) Assignee: SENSILE MEDICAL AG, Olten (CH)

( * ) Notice: Subject to any disclaimer, the term of this patent is extended or adjusted under 35 U.S.C. 154(b) by 746 days.

(21) Appl. No.: 14/379,338

(22) PCT Filed: Feb. 15, 2013

(86) PCT No.: PCT/IB2013/051240
§ 371 (c)(1),
(2) Date: Aug. 18, 2014

(87) PCT Pub. No.: WO2013/121390
PCT Pub. Date: Aug. 22, 2013

(65) Prior Publication Data
US 2015/0011939 A1    Jan. 8, 2015

(30) Foreign Application Priority Data

Feb. 17, 2012 (EP) ..................... 12156061

(51) Int. Cl.
*A61M 1/00* (2006.01)
*A61M 5/148* (2006.01)
(Continued)

(52) U.S. Cl.
CPC ...... *A61M 5/1483* (2013.01); *A61M 5/14236* (2013.01); *A61M 5/14244* (2013.01);
(Continued)

(58) Field of Classification Search
CPC .... A61M 2005/14573; A61M 5/14236; A61M 5/14212
(Continued)

(56) References Cited

U.S. PATENT DOCUMENTS 8,282,366 B2    10/2012    Hilber et al.
2004/0101426 A1*   5/2004   Wahlberg ............... F04C 9/007
                                                          417/492
(Continued)

FOREIGN PATENT DOCUMENTS

| WO | WO 01/085232 | 11/2001 |
| WO | WO 2007/074363 | 7/2007 |
| WO | WO 2011/119464 | 9/2011 |

OTHER PUBLICATIONS

Written Opinion in International Application No. PCT/IB2013/051240, dated Jul. 23, 2013, pp. 1-6.

*Primary Examiner* — Phillip Gray
(74) *Attorney, Agent, or Firm* — Saliwanchik, Lloyd & Eisenschenk (57) ABSTRACT

The invention relates to a liquid storage and delivery system including a reusable housing (8) comprising a control and drive unit, a container (2), a pump module (4) fluidically connected to the container (2), and a coupling system (6) configured for removably coupling the pump module (4) to the control and drive unit (6). The pump module comprises a pump engine (20), a pump outlet (22), and a transmission input coupling (18) coupled to the pump engine (20). The housing comprising the control and drive unit also comprises a pump drive (34) configured to engage the transmission input coupling (18) of the pump module (4) when the pump module (4) is coupled to the housing comprising the control and drive unit. The container (2) is in the form of a flexible pouch and the pump module (4) is permanently integrated with the flexible pouch and forms therewith a disposable unit.

11 Claims, 4 Drawing Sheets

(51) Int. Cl.
*A61M 5/142* (2006.01)
*A61M 5/145* (2006.01)
(52) U.S. Cl.
CPC ............ *A61M 2005/14268* (2013.01); *A61M 2005/14272* (2013.01); *A61M 2005/14506* (2013.01); *A61M 2005/14573* (2013.01)
(58) Field of Classification Search
USPC ........................................................ 604/151
See application file for complete search history.

(56) References Cited

U.S. PATENT DOCUMENTS

| | | |
|---|---|---|
| 2006/0100580 A1 | 5/2006 | Muller |
| 2007/0244435 A1 | 10/2007 | Hicks |
| 2009/0123309 A1 | 5/2009 | Hilber et al. |

* cited by examiner

LIQUID STORAGE AND DELIVERY SYSTEM

CROSS-REFERENCE TO RELATED APPLICATION

This application is the U.S. national stage application of International Patent Application No. PCT/IB2013/051240, filed Feb. 15, 2013.

The present invention relates to a liquid storage and delivery system comprising a container in the form of a flexible pouch, in particular for medical applications, such as for infusion or administration of a liquid to a patient. The present invention may also be used for storing and dispensing fluids in non-medical applications.

The use of flexible pouches for the storage and delivery of liquids has various advantages, depending on the application. The ability of a flexible container to change shape or conform to the pressures applied is very useful in many applications, as it allows the volume of liquid in the container to vary without the movement of a piston or membrane, or without the introduction of air into the container, which may contaminate or oxidize the liquid, to compensate for the change in volume. Another advantage is the low weight and low material use, which has, inter alia, environmental benefits.

Certain flexible infusion containers used in medical treatment work by drip-feeding, making use of gravity. The flexible container containing the solution is connected via a tube containing a valve to the patient and fixed above the patient by means of an intravenous (IV) pole or stand, in order to make use of gravity to ensure the flow of the liquid to the patient and avoid air entering into the catheter connected to the patient. In case the patient has to move the IV pole must be taken with. This is cumbersome and limits the mobility of the patient.

In case there is an emergency in the field, often the flexible pouch containing the liquid to be supplied to the patient has to be held up manually, in order to be positioned above the patient. Handling of the patient thus requires additional assistance that could be used for other tasks that are essential in an emergency situation where all the available manpower is needed.

It is known to connect a pump to a flexible container or pouch via a supply tube with an inlet and an outlet, whereby the inlet of the supply tube is connected to the flexible container and the outlet is connected to the pump. From the pump the liquid is then supplied via an intravenous tube to the patient. These pumps are generally reusable, having an interface where a user or even a patient can adjust the pumped volume supplied in a certain period. The pouch, the supply tube and the intravenous tube are disposed of after the use. A disadvantage is that the arrangement of the pump requires the connection of the supply tube to the pouch and the pump, which presents a risk of false manipulation and contamination. Moreover, the parts of the pump which come in contact with the drug need to be cleaned and sterilized after every use.

An object of this invention is to provide a liquid storage and delivery system comprising a flexible pouch, which is economical, versatile and easy to use.

For medical applications, an object of this invention is to provide a liquid storage and delivery system comprising a flexible pouch, which is economical, sterile, safe and easy to use.

For certain applications it is advantageous to provide a liquid storage and delivery system which is easily portable and autonomous.

It is advantageous to provide a liquid storage and delivery system with a single-use flexible pouch that is easily disposable with a low negative environmental impact.

It is advantageous to provide a liquid storage and delivery system that is economical to manufacture and handle.

It is advantageous to provide a liquid storage and delivery system that is light and compact.

Disclosed herein is a liquid storage and delivery system including a reusable control and drive unit, a container, a pump module fluidically connected to the container, and a coupling system. The coupling system is configured for removable coupling of the pump module to the control and drive unit. The pump module comprises a pump engine, a pump outlet, and a transmission input coupling coupled to the pump engine. The control and drive unit comprises a pump drive configured to engage the transmission input coupling of the pump module when the pump module is coupled to the control and drive unit. The container is in the form of a flexible pouch and the pump module is permanently integrated with the flexible pouch and forms therewith a disposable unit.

A user of the liquid storage and delivery system can operate the system via a user interface provided on the control and drive unit. The liquid storage and delivery system may be used for supplying liquid by pumping liquid out of the pouch, e.g., in a medical application to intravenously provide a liquid drug to a patient. The system may, in a variant, also be used to collect liquid in the pouch, e.g., in a medical application to collect blood from a donor.

The use of a disposable unit comprising all parts in contact with the liquid allows sterile and safe delivery or collection of fluid. An advantage of the direct mounting and connection of the pump module to the flexible pouch is that fewer steps are necessary in order set up an intravenous treatment of a patient, compared to conventional systems. No interconnection of a supply tube between the flexible pouch and a pump is necessary.

The liquid storage and delivery system can comprise a non-return valve in order to avoid drawing liquid or air into the container when the pump module is switched off or not in use. Alternatively, the pump module may be configured such that reverse flow is blocked.

In an advantageous embodiment the liquid storage and delivery system is configured as a portable device in which the control and drive unit may comprise an autonomous power source.

An advantage is the versatile use of the liquid storage and delivery system. Due to the integrated forming of the pump module on the pouch, the delivery system can be used in many orientations and positions without relying on gravity or external pressure generation means. For instance, in a medical emergency in the field, no IV pole is necessary in order to supply the liquid to the patient (even though an IV pole may be used if desired).

The pump module may be configured to pump out a liquid contained in the flexible container through the pump outlet, or to pump liquid from an external source into the flexible container, or a combination or both pumping in and pumping out depending on the mode of operation.

In an advantageous embodiment the coupling system comprises a releasable locking mechanism configured to lock the control and drive unit to the pump module when the pump module is coupled to the control and drive unit. The connection between the control and drive unit and the pump module may thus be secured during use.

The coupling system may further comprise a guide system configured to axially align a transmission output coupling of the control and drive unit to the transmission input coupling, thus assisting the easy engagement and coupling of the transmission output coupling with the transmission input coupling.

The guide system may comprise a pump module receiving cavity.

In an advantageous embodiment the transmission output coupling may be in the form of a toothed, splined or non-cylindrical shaft engaging a complementary recess or cavity in the transmission input coupling for the transfer of torque.

In an advantageous embodiment the pump module is configured as a rotary pump and the pump engine comprises a rotor rotatably movable in a stator and coupled to the transmission input coupling.

A liquid storage and delivery system according to an advantageous embodiment may include a pump module comprising a rotor and a stator according to the micropump configuration disclosed in WO 2007/074363.

The rotor may advantageously be directly attached to or integrally formed with the transmission input coupling, thus providing an efficient power train.

The stator may advantageously be attached to the flexible pouch via a pump fixing interface integrally formed with or directly attached to the stator.

In an advantageous embodiment the rotor is rotatably and axially movable to effect the pumping operation and interacts with sealings formed on the stator.

In an advantageous embodiment the guide system may comprise a guide rail portion formed on the control and drive unit and a complementary guide rail portion attached to the flexible pouch. The guide rail portions interact with one another during the connection of the control and drive unit to the pump module to guide the two together. The guide rail portions may extend parallel with the transmission output and the transmission input coupling when the control and drive unit is connected to the pump module.

The complementary rail portion and a pump fixing interface, via which the stator of the pump engine is attached to the flexible pouch, may advantageously be integrally formed with and permanently attached to the flexible pouch.

In an advantageous embodiment the pump outlet may be axially aligned with the transmission input coupling and the rotor. The longitudinal axis of the rotor may also be aligned with the longitudinal axis of the pump outlet and the transmission input coupling.

In another advantageous embodiment the pump fixing interface may be directly connected to the pouch by welding it in between two sheets of the flexible pouch. The pump outlet may be directed perpendicular or transversely to a longitudinal axis of the rotor Advantageously a longitudinal axis of a pump module receiving cavity of the guide system may extend axially aligned with the longitudinal axis of the rotor and may contain at least a part of the locking mechanism to secure the connection between the control and drive unit and the pump module.

Further objects and advantageous features of the invention will be apparent from the claims, detailed description, and annexed drawings, in which:

Referring to the figures, which show exemplary embodiments of the invention, a liquid storage and delivery system 1 comprises a pump module 4 and a flexible container 2 in the form of a pouch. The pump module 4 is permanently integrated with the flexible container 2 and forms therewith a disposable unit. A housing 8 comprising a reusable control and drive unit can be temporarily connected to the pump module 4. The housing also comprises a pump module receiving cavity 60, a user interface 32 and a power source. For portable applications, the power source is preferably an autonomous on-board power source such as a battery. The control and drive unit may also be powered by an external power source.

Figure 1:
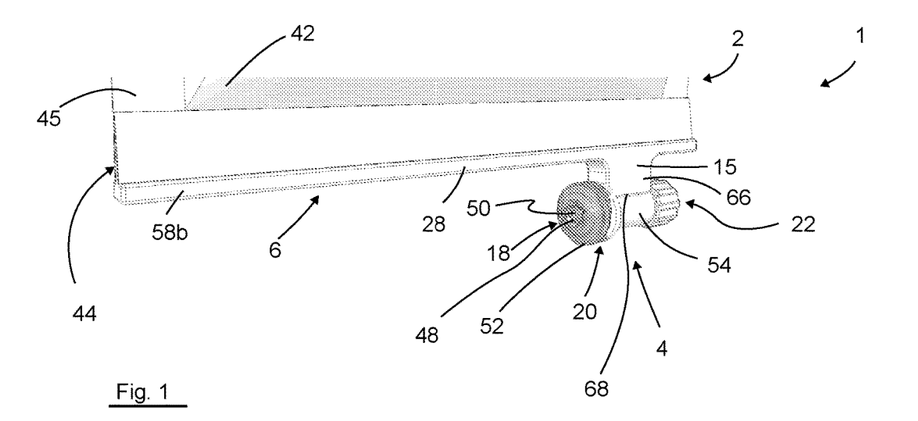
FIG. 1 is a perspective view of an integrated pump module and flexible pouch of a liquid storage and delivery system according to an embodiment of the invention.

The housing 8 comprising a control and drive unit also comprises a pump drive 34 comprising a transmission output coupling 35. The transmission output coupling 35 may be in the form of a mechanical coupling such as a splined, toothed, or non-cylindrical shaft which engages with a transmission input coupling 18 formed on a pump engine 20 of the pump module 4 to transmit torque. The transmission input coupling 18 may be in the form of a recess with teeth as shown in FIG. 1, in which a shaft including complementary teeth of the transmission output coupling 35 may glide in during the connection of the housing comprising the control and drive unit to the pump module 4. When the housing comprising the control and drive unit is connected, the shaft may engage with the recess and the teeth therein, in order to transfer a torque or force from the pump drive 34 to the pump engine 20. A mechanical coupling between the pump drive 34 and the pump engine 20 may also include a gear box or other torque multiplication or reduction mechanism arranged between the transmission output coupling 35 and the pump engine 20.

In a variant the pump drive 34 and the transmission output coupling 35 may be coupled by a magnetic coupling. In a variant of magnetic coupling, the pump drive 34 may correspond to an electromagnetic stator drive transferring torque by an electromagnetic field to the transmission input coupling of the rotor that may comprise permanent magnets. The pump drive 34 may comprise, in many variants, an electrical motor.

The pump engine 20 may comprise a rotor 52 and a stator 54 whereby the rotor 52 is attached to the transmission input coupling 18. In an advantageous variant the pump engine 20 may have the function and features of a micropump such as disclosed in WO 2007/074363.

It is advantageous to provide a liquid storage and delivery system comprising a pump module 4 including a rotary pump. Other pump solutions, however, are possible.

The housing or stator 54 may be fixed to or integrally formed with a pump interface 15, which may advantageously be directly sealingly fixed to the flexible container or pouch 2 by welding, for instance thermal or ultrasonic welding. Other sealed attachment solutions, however, may also be employed in variants of the invention, such as bonding by means of an adhesive, or by mechanical clamping means.

The stator 54 may advantageously be attached to the pump fixing interface by being integrally formed therewith. In a variant, the pump fixing interface and housing or stator of the pump module may also be formed of separate components that are attached together by welding, bonding or mechanical fixing means.

Figure 2:
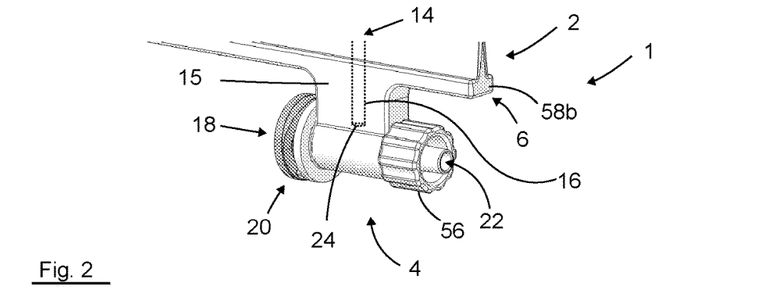
FIG. 2 is a similar perspective view of an embodiment according to FIG. 1, where a pump outlet of the pump module is visible.
Figure 3:
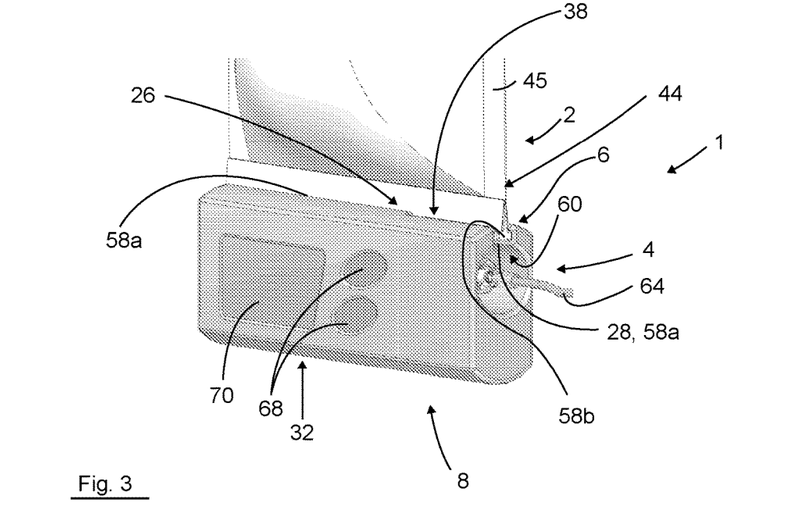
FIG. 3 is a perspective view of a liquid storage and delivery system according to an embodiment of the invention.

The pump fixing interface 15 may comprise part of a coupling system 6, such as shown in form of a complementary guide rail portion 58b in FIGS. 1, 2 and 3 that is slidably received in a guide rail portion 58a on the housing comprising the control and drive unit.

It is also possible to avoid using guide rail portions 58a, 58b and connect the housing comprising the control and drive unit to the pump module 4 such that the control and drive unit attaches directly to the pump module. In this case, the pump module receiving cavity 60 may provide a guiding function to ensure easy and correct engagement of the pump module transmission input coupling 18 to the transmission output coupling 35 of the pump drive mounted in the control and drive unit.

The pump module receiving cavity 60 may comprise latches of a locking mechanism 26, for releasably securing the connection between the housing comprising the control and drive unit and the pump module 4.

The pump fixing interface 15 may have the form of an extension integrally formed with the pump module stator and the means for sealing attachment to the flexible pouch. In the embodiment of FIGS. 1, 2 and 3 the guide rail portion 58b is welded along a seam of the flexible pouch and integrally formed with the pump fixing interface 15. In the embodiment of FIGS. 5 to 8, the pump fixing interface 15 integrally formed with the pump module stator comprises an attachment surface 47 onto and around which opposed sheets of flexible membrane 42 may be sealingly glued or welded, to hermetically enclose the pump inlet 24 with the interior of the flexible pouch.

In a variant of the invention, the pump module may be attached to the flexible pouch in a position distant from the border region or seam, for instance by means of a flange (not shown) welded, bonded or clamped to the membrane of the flexible pouch, the flange forming the pump fixing interface 15 to which the stator or housing of the pump module 4 is integrally formed or fixed.

The pump module 4 further comprises a pump outlet 22. This pump outlet 22 may for instance comprise a Luer connector or another type of sealed connector for fluidic connection. The pump outlet 22 may be connected to a supply or suction tube 64 which, in a medical application, may be connected to a patient via a catheter. In other variants, instead of the supply or suction tube 64 connected to the pump outlet 22, it is possible to have a nozzle or dispenser (not shown) connected to the pump outlet 22. This may, for instance, be useful for dispensing cosmetic liquids or soaps or other liquids contained in the flexible pouch. The term "pump outlet" as used herein should be understood to also include the function of a pump inlet for applications where the pump module draws liquid into the flexible pouch. Applications in the medical field may include collection of blood from a donor. Applications in non-medical fields may include the collection of a variety of liquid samples for testing purposes (e.g., chemicals, water) or liquid products for storage and transport and later use.

In a variant (not shown) the coupling system 6 may comprise a magnetic coupling to facilitate the coupling of the housing comprising the control and drive unit to the pump module 4 instead of or in addition to mechanical guiding and locking systems.

Referring specifically to FIGS. 1, 2, 3, 4, 6, 7 and 8, further details of the specific embodiments illustrated and their operation will now be described. FIG. 1 shows the liquid storage and delivery system 1 with the flexible container 2 in the form of a flexible pouch comprising a flexible membrane 42. Integrated with the flexible pouch is the pump module 4 which is connected to the pouch via a pump fixing interface 15. The pump fixing interface 15, which may advantageously be made of an injected or molded polymer, comprises a fixing extension 66 having a free end 68 to which the pump module 4 is attached, e.g., glued, welded or mechanically fixed.

Integrally formed on the end of the pump fixing extension 15 oriented toward the flexible pouch is the complementary guide rail portion 58b extending parallel to the border region 44 of the flexible pouch. The complementary guide rail portion 58b is welded to the flexible pouch via an end region directed towards the flexible pouch. The border region 44 of the flexible pouch is thereby arranged in between two parts of the end region of the complementary guide rail portion 58b. It may also be possible to weld or glue the border region 44 of the flexible pouch to one side of the end region of the complementary guide rail portion 58b. The complementary guide rail portion 58b engages with a guide rail portion 58a of the housing comprising the control and drive unit (FIG. 3).

The border region 44 of the flexible pouch comprises a seam 45, for instance a welding seam 45 that hermetically seals the two flexible sheets of the flexible pouch together. The sheet or sheets forming the flexible pouch may be of a polymer material dependent on the application and liquids to be stored as known in the packaging industry. In a variant the end region of the complementary guide rail portion 58b is attached or welded to the seam 43 of the border region 4 of the flexible pouch.

Figure 4:
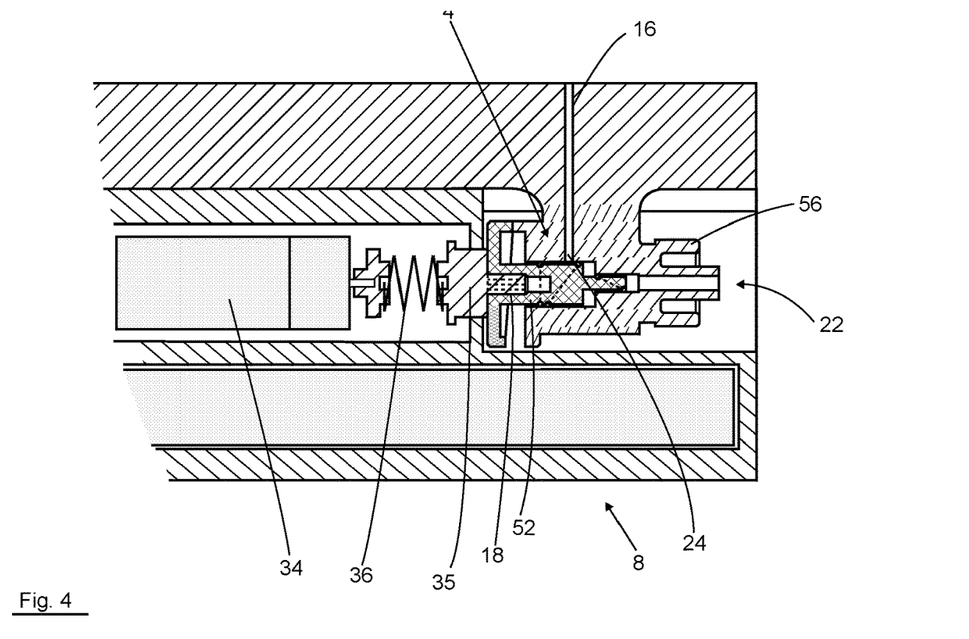
FIG. 4 is a cross-section of part of the embodiment according to FIGS. 1-3 illustrating the pump module coupled to the drive of the control unit.

FIG. 1 further shows the transmission input coupling 18 attached to the rotor 52 of the pump engine 20. The transmission input coupling 18 comprises a recess 48 with teeth. The recess 48 extends inward toward the rotor 52 and substantially parallel to the complementary guide rail portion 58b and is axially aligned to the longitudinal axis of the rotor 52 and the pump outlet 22. The recess 48 further extends substantially parallel to the shaft of the transmission output coupling 35, when the housing comprising the control and drive unit is connected to the pump module 4 (FIGS. 3 and 4). The longitudinal axis of the shaft and the rotor 52 are thereby axially aligned and connected to one another via complementary teeth of the shaft which engage with the teeth of the recess 48.

The rotor 52 of the pump engine 20 is rotatably movable and housed in the stator 54. The rotor 52 and transmission input coupling 18 may advantageously be made of injected or molded polymer, either integrally formed as a single molding or as separate elements attached together. The stator 54 forms a pump housing portion, which may advantageously be made of an injected or molded polymer. In an advantageous embodiment the pump module 4 may comprise the features of the micropump described in WO 2007/074363, whereby the rotor 52 is axially movable and comprises channels arranged on two different diameters of the rotor shaft that interact with sealings arranged on the stator 54 to form valves that open and close as a function of the rotation and axial displacement of the rotor that causes a pumping action.

The recess 48 comprises a guide surface 50 partially in the form of a funnel in order to guide the shaft of the transmission output coupling 35 during the connecting operation of the housing comprising the control and drive unit to the pump module 4.

FIG. 2 shows the pump module 4 whereby the pump outlet 22 is visible. The pump outlet 22 comprises a connector for fluid coupling, such as a Luer connector 56. The pump outlet 22 is fluidically connected to the interior zone of the flexible pouch via the pump engine 20, a pump module inlet 24 and via a passage portion 16 arranged in the pump fixing interface 15, said passage portion 16 connecting the pump inlet 24 with the interior zone of the flexible pouch via an outlet 14 of the pouch.

FIG. 3 shows the liquid storage and delivery system with the housing comprising the control and drive unit connected to the disposable unit formed by the pump module 4 and the flexible container or pouch 2. The seam 45 of the border region 44 is shown. FIG. 3 further shows how the guide rail portion 58a formed on housing comprising the control and drive unit interacts with the complementary guide rail portion 58b of the coupling system 6. The guide rail portion 58a is formed as a groove; however, a kinematic inverse solution is also possible, meaning that the complementary guide rail portion 58b may be formed as a groove.

The guide rail portion and the complementary guide rail portion 58a, 58b are part of a guide system 28 of the coupling mechanism or system 6. The coupling system 6 further comprises a releasable locking mechanism 26. Said releasable locking mechanism 26 may contain latches formed on housing comprising the control and drive unit, said latches engaging with complementary latches formed, for instance, on the housing or stator of the pump module 4, the pump fixing interface 15, or the complementary guide rail portion 58b.

In FIG. 3 the supply or suction tube 64 is connected to the pump outlet 22. In a variant a Luer connector is used in order to facilitate the connecting operation. When the housing comprising the control and drive unit is connected to the pump module 4 and the flexible pouch, the pump module 4 slides into the pump module receiving cavity 60, said pump module receiving cavity 60 thereby guiding and aligning the shaft with the recess 48 so that they can smoothly connect. The pump module receiving cavity 60 protects the pump module 4 from external impacts when the housing comprising the control and drive unit is completely connected to the disposable unit.

The housing 8 comprising the control and drive unit also comprises the user interface 32 allowing a user to control the liquid storage and delivery system 1. The user interface 32 comprises control buttons 68 and a screen 70, said screen 70, for example, showing the amount of liquid pumped in a certain time period. A user may activate the delivery or pumping via the control buttons 68. The control buttons 68 may also be used to program certain functions of the control electronics included in housing containing the control and drive unit.

In order to facilitate the insertion of the rail portion 58a of the housing comprising the control and drive unit into the complementary rail portion 58b of the coupling system 6, the housing includes a funnel section 38 which is slightly wider than the guide rail portion 58a. This makes it easier to connect the control and drive unit in the housing to the pump module 4.

FIG. 4 shows a cross section through a connection between the pump module 4 and the housing comprising the drive and control unit. The pump drive 34 is connected to the transmission output coupling 35 via means that ensure the transmission of torque. In the embodiment shown, a spring 36 provides the coupling for torque transmission between the motor 34 and the transmission output coupling 35 as well as allowing an axial resilient displacement to facilitate and ensure a good plugging connection of the pump module to the drive, namely the insertion of the toothed shaft of the transmission output coupling 35 into the complementary toothed cavity of the pump module transmission input coupling 34. Advantageously, the spring 36 provides some resilient rotational and axial adjustment to allow the teeth of the plugging connection to be rotationally aligned and slide axially into full engagement. In addition to or in replacement of the spring, the pump drive 34 may comprise a shaft, e.g., a splined shaft, for the transmission of torque to the transmission output coupling 35.

Figure 5:
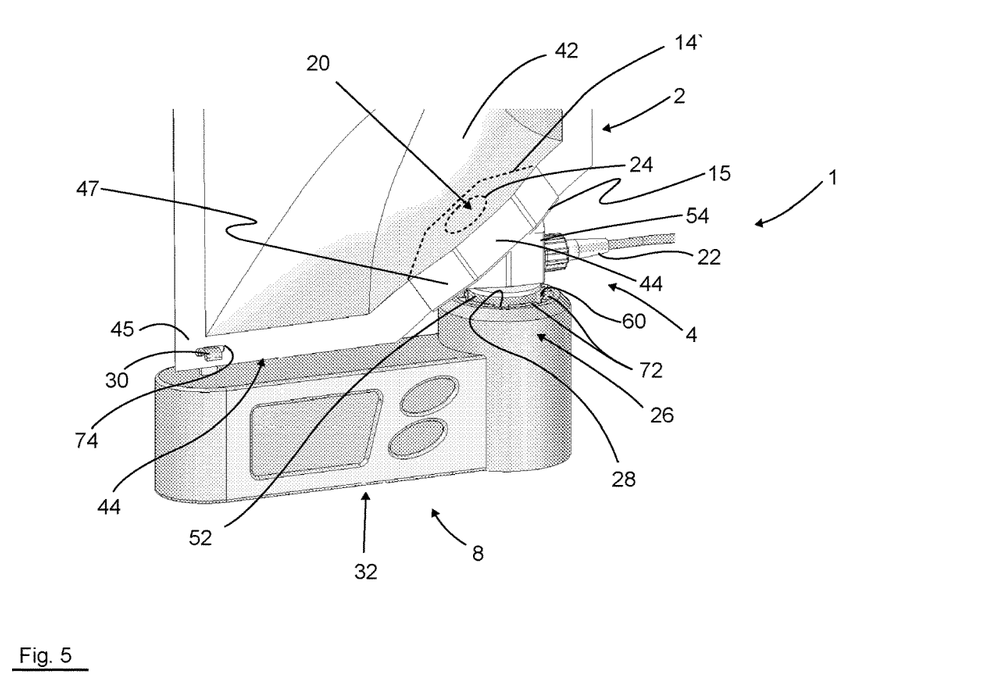
FIG. 5 is a perspective view of a liquid storage and delivery system according to another embodiment of the invention.

FIG. 5 shows another variant of the present invention. The pump fixing interface 15 is formed preferably as a rhombic or similar elongated shaped body which is integrally formed with—or connected to—the stator 54 of the pump engine 20 and provided with a surface configured to be sandwiched between two sheets of a flexible membrane 42 at the seam 45 and hermetically (sealingly) glued or welded to said sheets of the flexible membrane 42. The pump module 4 is thus directly mounted at an outlet 14 of the flexible pouch. The pump engine 20 is directly and fluidically connected to the interior volume of the flexible pouch via the pump inlet 24. The pump module 4 is for certain applications preferably welded to the flexible container 2. Advantages of welding are the low cost, good sealing and avoidance of material compatibility issues with the liquid or drug contained in the pouch that can be caused, for instance, by adhesive bonding materials.

The embodiment according to FIG. 5 shows the pump module 4 arranged in a corner of the border region 44 of the flexible pouch. It is, however, possible to mount the pump module 4 in another position along the border region 44 of the flexible container.

The diamond-shaped surface or body 15 may also have any other shape, such as circular, oval, etc.

The housing comprising the control and drive unit also comprises the pump module receiving cavity 60, which also serves as part of the guide system 28. A part of the releasable locking mechanism 26 is advantageously arranged within the pump receiving cavity 60 in the form of latches 72 and the other part of the releasable locking mechanism 26 advantageously on the stator 54 in the form of complementary latches. In a variant, the latches may be part of a bayonet mechanism where the housing comprising the control and drive unit is connected to the pump module 4 by a pivoting movement.

In the embodiment according to FIG. 5, the pump outlet 22 is oriented perpendicular to the longitudinal axis of the pump rotor 52. A longitudinal axis of the pump module receiving cavity 60 is aligned with the longitudinal axis of the rotor 52 when the housing comprising the control and drive unit is connected to the pump module 4.

The housing comprising the control and drive unit further comprises a coupling portion 30 in the form of a fixing hook which engages with a cutout 74 arranged in the border region 44, preferably in the seam 45 of the flexible container or the flexible pouch. The cutout 74 and the coupling portion 30 may thereby form part of the releasable locking mechanism 26.

Figure 6:
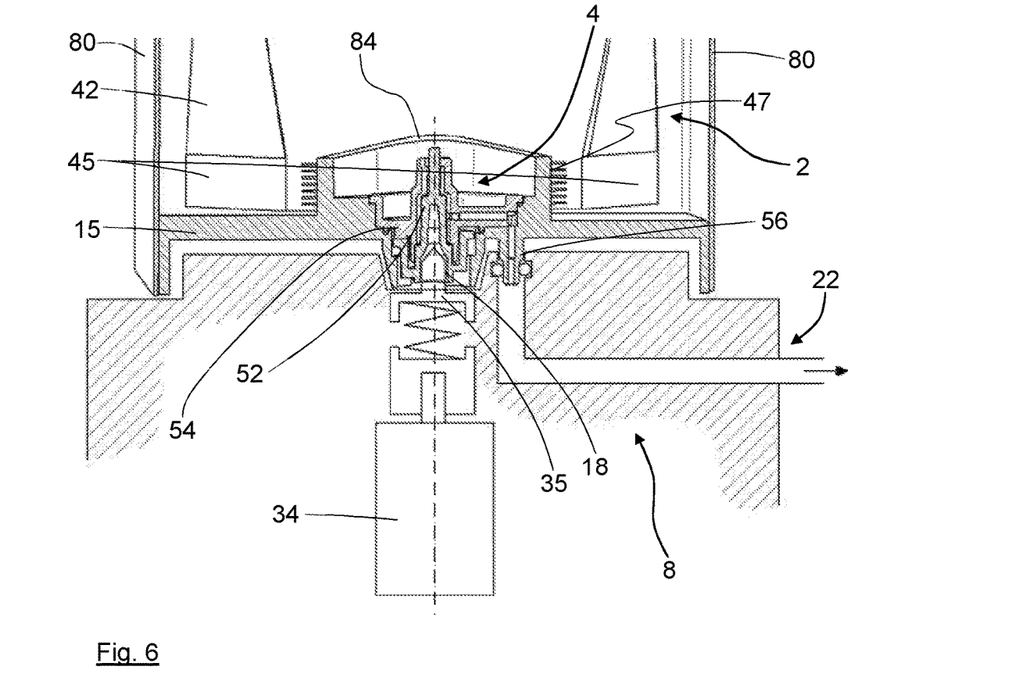
FIG. 6 is a perspective view of a liquid storage and delivery system according to another embodiment of the invention.

FIG. 6 shows the liquid storage and delivery system 1 with the pump module 4 integrated in the flexible pouch 2. The embodiment shown in FIG. 6 does thus not comprise a passage portion 16 (see FIG. 4).

Figure 7:
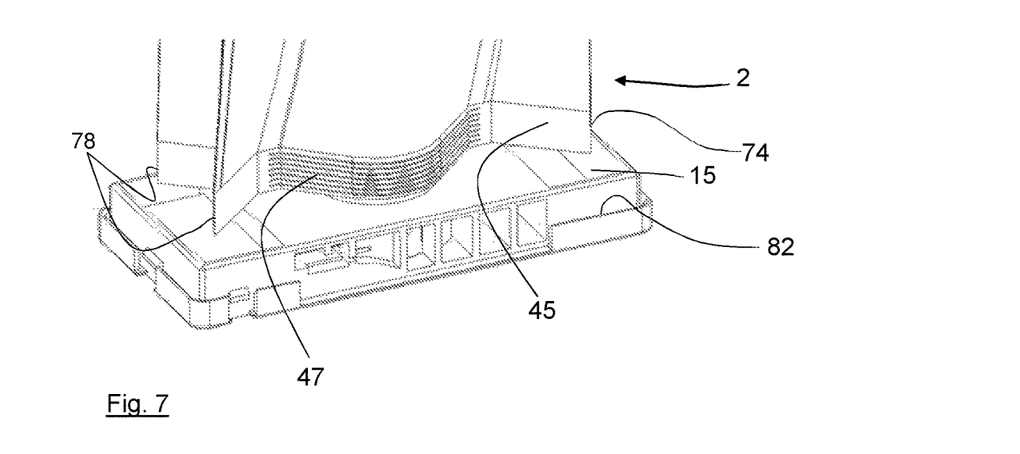
FIG. 7 is a perspective view of a liquid storage and delivery system similar to the one shown in FIG. 6.
Figure 8:
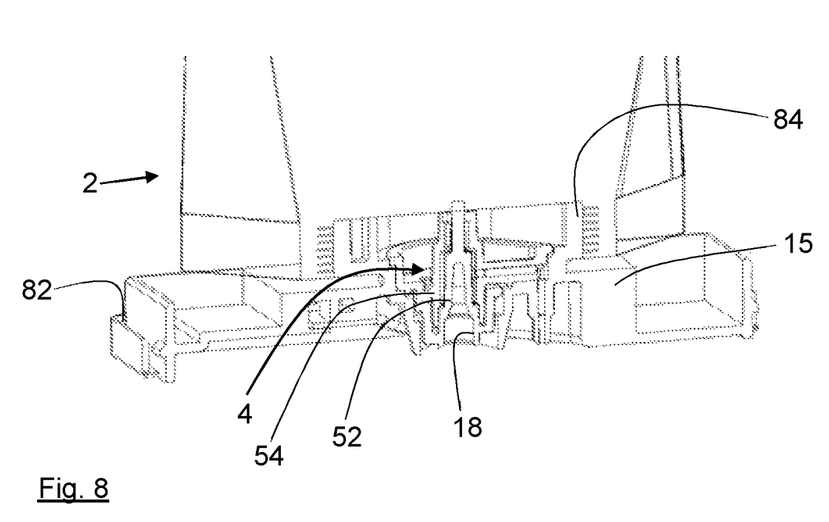
FIG. 8 is a perspective view of a liquid storage and delivery system with a partially cut pump fixing interface.

One end of the pump module 4 extends into the flexible pouch 2. The membranes 42 of the flexible pouch 2 are directly welded onto the attachment surface 47 of the pump fixing interface 15. The pump module 4 is arranged centrally at a lower end of the flexible container 2. As best illustrated in FIGS. 7 and 8, the flexible container 2 comprises the welding seams 45 which are connected in a way so that the edges of the seams 45 form four corner portions 78. These corner portions 78 provide additional stability to the connection between pump fixing interface 15 and the flexible container 2.

The attachment surface 47 is formed on an outer side of a collar portion 84 of the pump fixing interface 15. The collar portion 84 is configured to extend towards and in some cases partially into the flexible pouch 2 so that it may protect the pump module 4.

The pump fixing interface 15 may be configured to be connected to the housing comprising the control and drive unit as illustrated in FIG. 6.

As shown in FIG. 6, the pump fixing interface 15 may be configured to receive a housing guard 80 or the like to protect the flexible container 2 during use and transport. The housing guard 80 may be configured to be connected to the pump fixing interface 15 via a circumferential shoulder 82 arranged along the periphery of the pump fixing interface 15, as best illustrated in FIG. 7.

The invention claimed is:

1. A liquid storage and delivery system including a reusable control and drive unit, a container, a pump interface sealingly fixed to the container, a pump module fluidically connected to the container, and a coupling system configured for removably coupling the pump module to the control and drive unit, the pump module comprising a rotary pump engine comprising a stator fixed to or integrally formed with the pump interface and a rotor rotatably movable in the stator, and a pump outlet, the coupling system comprising a transmission input coupling coupled to the rotor of the pump engine, the control and drive unit comprising a pump drive configured to mechanically engage the transmission input coupling of the pump module when the pump module is coupled to the control and drive unit, wherein the container is in the form of a flexible pouch and the pump module is arranged external to the flexible pouch and forms therewith a disposable unit, and wherein the rotor of the rotary pump engine is further axially movable during a pumping operation mode.

2. The liquid storage and delivery system according to claim 1, configured as a portable device comprising a control unit, a drive unit and an autonomous power source.

3. The liquid storage and delivery system according to claim 1, wherein said pump module is configured to pump a liquid contained in the flexible container through the pump outlet.

4. The liquid storage and delivery system according to claim 1, wherein said pump module is configured to pump a liquid into the flexible container through the pump outlet.

5. The liquid storage and delivery system according to claim 1, wherein the coupling system comprises a releasable locking mechanism configured to lock the control and drive unit to the pump module when the pump module is coupled to the control and drive unit.

6. The liquid storage and delivery system according to claim 1, wherein the coupling system comprises a guide system configured to axially align a transmission output coupling of the control and drive unit to the transmission input coupling.

7. The liquid storage and delivery system according to claim 1, wherein the guide system comprises a pump module receiving cavity.

8. The liquid storage and delivery system according to claim 1, wherein the transmission output coupling is in the form of a shaft.

9. The liquid storage and delivery system according to claim 1, wherein the rotor is directly attached to the transmission input coupling.

10. The liquid storage and delivery system according to claim 1, wherein the stator is attached to the flexible pouch via an integral pump fixing interface.

11. The liquid storage and delivery system according to claim 1, wherein the pump fixing interface is directly connected to the pouch by welding it in between two sheets of the flexible pouch and wherein the pump outlet is arranged perpendicular to a longitudinal axis of the rotor.

* * * * *